United States Patent
Choi et al.

(10) Patent No.: US 12,272,065 B2
(45) Date of Patent: Apr. 8, 2025

(54) APPARATUS AND METHOD FOR IMAGE SEGMENTATION

(71) Applicant: RESEARCH COOPERATION FOUNDATION OF YEUNGNAM UNIVERSITY, Gyeongsangbuk-do (KR)

(72) Inventors: Gyu Sang Choi, Daegu (KR); Hyun Kwang Shin, Gyeongsangbuk-do (KR)

(73) Assignee: RESEARCH COOPERATION FOUNDATION OF YEUNGNAM UNIVERSITY, Gyeongsangbuk-do (KR)

( * ) Notice: Subject to any disclaimer, the term of this patent is extended or adjusted under 35 U.S.C. 154(b) by 422 days.

(21) Appl. No.: 17/723,767

(22) Filed: Apr. 19, 2022

(65) Prior Publication Data
US 2023/0005152 A1    Jan. 5, 2023

(30) Foreign Application Priority Data
Feb. 24, 2021    (KR) .................. 10-2021-0024711

(51) Int. Cl.
G06T 7/10    (2017.01)

(52) U.S. Cl.
CPC ...... *G06T 7/10* (2017.01); *G06T 2207/10088* (2013.01); *G06T 2207/20084* (2013.01); *G06T 2207/30016* (2013.01); *G06T 2207/30096* (2013.01)

(58) Field of Classification Search
CPC ..... G06T 7/10; G06T 7/11; G06T 7/12; G06T 2207/20081; G06T 2207/20084; G06T 2207/10088; G06T 2207/30016; G06T 2207/30096; G06N 3/02–0985
See application file for complete search history.

(56) References Cited

FOREIGN PATENT DOCUMENTS
KR    10-2094320 B1    3/2020

OTHER PUBLICATIONS

Ronneberger, Olaf, Philipp Fischer, and Thomas Brox. "U-net: Convolutional networks for biomedical image segmentation." MICCAI 2015: 18th international conference, Munich, Germany, Oct. 5-9, 2015, proceedings, part III 18. Springer International Publishing, 2015. (Year: 2015).*

Cao, Yue, et al. "GCNet: Non-Local Networks Meet Squeeze-Excitation Networks and Beyond." 2019 IEEE/CVF International Conference on Computer Vision Workshop (ICCVW). IEEE, 2019. (Year: 2019).*

(Continued)

*Primary Examiner* — Geoffrey E Summers
(74) *Attorney, Agent, or Firm* — The PL Law Group, PLLC (57) ABSTRACT

An apparatus for image segmentation according to an embodiment includes an acquirer configured to acquire one or more images in which an object is photographed and a segmentation performer configured to perform segmentation on the one or more images using a segmentation model which is deep learned through a plurality of images, in which the segmentation model is a U-Net-based model including a first type module based on depth-wise separable convolution (DSC) and a second type module based on global context network (GCNet).

14 Claims, 7 Drawing Sheets

(56) References Cited

OTHER PUBLICATIONS

Qi, Kehan, et al. "X-net: Brain stroke lesion segmentation based on depthwise separable convolution and long-range dependencies. " MICCAI 2019: 22nd International Conference, Shenzhen, China, Oct. 13-17, 2019, Proceedings, Part III 22. Springer International Publishing, 2019. (Year: 2019).*

Li, Zhuoying, et al. "Memory-efficient automatic kidney and tumor segmentation based on non-local context guided 3D U-Net." MICCAI 2020: 23rd International Conference, Lima, Peru, Oct. 4-8, 2020, Proceedings, Part IV 23. Springer International Publishing, 2020. (Year: 2020).*

Siddique, Nahian, et al. "U-Net and its variants for medical image segmentation: theory and applications." arXiv preprint arXiv: 2011. 01118v1 (2020). (Year: 2020).*

Shin, Hyunkwang, et al. "Automated segmentation of chronic stroke lesion using efficient U-Net architecture." Biocybernetics and Biomedical Engineering 42.1 (2022): 285-294. (Year: 2022).*

Office action issued on May 18, 2023 from Korean Patent Office in a counterpart Korean Patent Application No. 10-2021-0024711 (all the cited references are listed in this IDS.) (English translation is also submitted herewith.).

Kehan Qi et al., "X-Net: Brain Stroke Lesion Segmentation Based on Depthwise Separable Convolution and Long-Range Dependencies", MICCAI 2019: 22nd International Conference (Oct. 10, 2019).

Jie Chen et al., "Road Crack Image Segmentation Using Global Context U-net", Proceedings of the 2019 3rd international conference on computer science and artificial intelligence (Mar. 4, 2020).

Zhuoying Li et al., "Memory-Efficient Automatic Kidney and Tumor Segmentation Based on Non-local Context Guided 3D U-Net", MICCAI 2020: 23rd International Conference (Sep. 29, 2020).

* cited by examiner

APPARATUS AND METHOD FOR IMAGE SEGMENTATION

GOVERNMENT LICENSE RIGHTS

This invention was made with Korean government support under Project No. NRF-2021R1A6A1A03039493 (Task Unique No. 1345334139, Name of Institution Managing Project: National Research Foundation, Research Task Name: Information and Communication Research Institute, Name of Institution Conducting Project: Yeungnam University) awarded by Ministry of Education, Republic of Korea and under Project No. 2019R1A2C1006159 (Task Unique No. 1711142173, Name of Institution Managing Project: National Research Foundation, Research Task Name: on Intelligent Information Analysis Platform for Automatic Fact Checking. Name of Institution Conducting Project: Yeungnam University) awarded by Ministry of Science and ICT, Republic of Korea. The Korean government has certain rights in the invention.

CROSS-REFERENCE TO RELATED APPLICATION(S)

This application claims the benefit under 35 USC § 119 of Korean Patent Application No. 10-2021-0024711, filed on Feb. 24, 2021, in the Korean Intellectual Property Office, the entire disclosure of which is incorporated herein by reference for all purposes.

BACKGROUND

1. Technical Field

The disclosed embodiments relate to a technology for improving training efficiency and performance of a deep learning model that performs image segmentation.

2. Background Art

Brain stroke is a symptom in which a part of the brain is damaged by rupture or blockage of a cerebral blood vessel, and is a cause of death that threatens the lives of people around the world. However, until recently, in order to determine a position where the brain stroke has occurred on a medical image, there is no choice but to rely on an opinion of a specialist, and thus it was difficult to respond immediately, and the accuracy was also relatively low.

Therefore, with the recent development of deep learning technology, network models such as SegNet and U-Net have been proposed for segmentation of the medical image, but (1) the number of training parameters was huge, and thus resources for training the model were wasted severely, (2) as training ng deepened, the problems of long-term dependencies became prominent, and (3) due to architectural structural limitations of the model, the results of lesion segmentation were often inaccurate.

SUMMARY

The disclosed embodiments are intended to improve an architecture of a deep learning model that performs image segmentation to enhance training efficiency and image segmentation performance of the model.

An apparatus for image segmentation according to an embodiment includes an acquirer configured to acquire one or more images in which an object is photographed, and a segmentation performer configured to perform segmentation on the one or more images using a segmentation model which is deep learned through a plurality of images, in which the segmentation model is a U-Net-based model including a first type module based on depth-wise separable convolution (DSC) and a second type module based on a global context network (GCNet).

The one or more images may include a tomographic image of a brain obtained by magnetic resonance imaging (MM).

The segmentation performer may be configured to segment the tomographic image of the brain into a plurality of sections, and determine one or more sections satisfying a preset condition among the plurality of sections as a stroke lesion.

The segmentation model may be a U-Net-based model in which at least some of a plurality of convolution layer blocks in the segmentation model are replaced with the first type module.

The segmentation model may be a U-Net-based model in which the second type module is disposed between an encoder in which down sampling is performed and a decoder in which up sampling is performed in the segmentation model.

The first type module may be configured to include a plurality of depth-wise convolution layer blocks for extracting feature information of a feature map and a plurality of point-wise convolution layer blocks for controlling the number of channels of the feature map.

The first type module may be configured to calculate a map for extracting feature information by repeatedly applying the depth-wise convolution layer block and the point-wise convolution layer block to an input feature map and calculate a map for controlling the number of channels by applying only the point-wise convolution layer block to the input feature map, and sum the map for extracting the feature information and the map for adjusting the number of channels and output a result of the summation.

The second type module may be configured to include a first convolution layer block for extracting feature information of a feature map, a second convolution layer block, and a global context block (GCBlock) based on the global context network.

The second type module may be configured to calculate a global feature map by applying the first convolution layer block, the second convolution layer block, and the global context block to an input feature map, and sum the input feature map and the global feature map and output a result of the summation.

A method for image segmentation according to another embodiment includes acquiring one or more images in which an object is photographed, and performing segmentation on the one or more images using a segmentation model which is deep learned through a plurality of images, in which the segmentation model is a U-Net-based model including a first type module based on depth-wise separable convolution (DSC) and a second type module based on a global context network (GCNet).

The one or more images may include a tomographic image of a brain obtained by magnetic resonance imaging (MM).

In the performing of segmentation, the tomographic image of the brain may be segmented into a plurality of sections, and one or more sections satisfying a preset condition among the plurality of sections may be determined as a stroke lesion.

The segmentation model may be a U-Net-based model in which at least some of a plurality of convolution layer blocks in the segmentation model are replaced with the first type module.

The segmentation model may be a U-Net-based model in which the second type module is disposed between an encoder in which down sampling is performed and a decoder in which up sampling is performed in the segmentation model.

The first type module may be configured to include a plurality of depth-wise convolution layer blocks for extracting feature information of a feature map and a plurality of point-wise convolution layer blocks for controlling the number of channels of the feature map.

The first type module may be configured to calculate a map for extracting feature information by repeatedly applying the depth-wise convolution layer block and the point-wise convolution layer block to an input feature map and calculate a map for controlling the number of channels by applying only the point-wise convolution layer block to the input feature map, and sum the map for extracting the feature information and the map for adjusting the number of channels and output a result of the summation.

The second type module may be configured to include a first convolution layer block for extracting feature information of a feature map, a second convolution layer block, and a global context block (GCBlock) based on the global context network.

The second type module may be configured to calculate a global feature map by applying the first convolution layer block, the second convolution layer block, and the global context block to an input feature map, and sum the input feature map and the global feature map and output a result of the summation.

According to the disclosed embodiments, by performing image segmentation using a layer for extracting feature information of a feature map and a layer for controlling the number of channels of the feature map in combination, the number of parameters to be trained on the model can be drastically reduced to improve training efficiency.

Further, according to the disclosed embodiments, by constructing a model for image segmentation based on the global context network so that non-local features can be reflected in training, the problems of long-term dependencies can be resolved when training the model.

DETAILED DESCRIPTION

Hereinafter, a specific embodiment will be described with reference to the drawings. The following detailed description is provided to aid in a comprehensive understanding of the methods, apparatus and/or systems described herein. However, this is illustrative only, and the disclosed embodiments are not limited thereto.

In describing the embodiments, when it is determined that a detailed description of related known technologies may unnecessarily obscure the subject matter of the present disclosure, a detailed description thereof will be omitted. In addition, terms to be described later are terms defined in consideration of functions in the disclosed embodiments, which may vary according to the intention or custom of users or operators. Therefore, the definition should be made based on the contents throughout this specification. The terms used in the detailed description are only for describing embodiments, and should not be limiting. Unless explicitly used otherwise, expressions in the singular form include the meaning of the plural form. In this description, expressions such as "comprising" or "including" are intended to refer to certain features, numbers, steps, actions, elements, some or combination thereof, and it is not to be construed to exclude the presence or possibility of one or more other features, numbers, steps, actions, elements, some or combinations thereof, other than those described.

Figure 1:
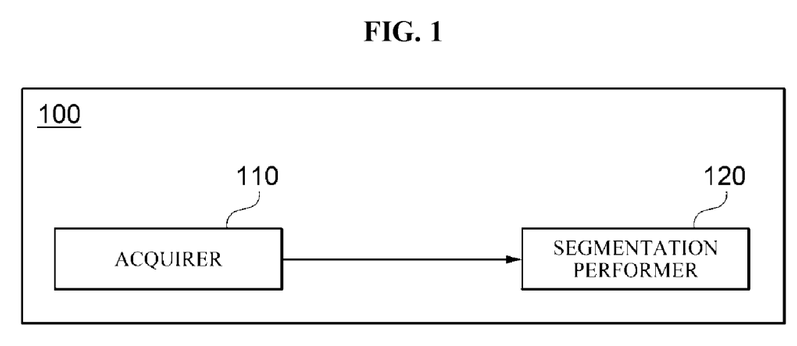
FIG. 1 is a block diagram illustrating an apparatus for image segmentation according to an embodiment.

FIG. 1 is a block diagram illustrating an apparatus 100 for image segmentation according to an embodiment.

As illustrated, the apparatus 100 for image segmentation according to an embodiment includes an acquirer 110 and a segmentation performer 120.

The acquirer 110 acquires one or more images in which an object is photographed.

According to an embodiment, the acquirer 110 may acquire one or more images including a tomographic image of a brain obtained by magnetic resonance imaging (MRI).

According to an embodiment, the acquirer 110 may acquire an image from a separate database (not illustrated) outside the apparatus 100 for image segmentation, but is not limited thereto, and may acquire an image from a storage space disposed inside the apparatus 100 for image segmentation (not illustrated). In addition, the acquirer 110 may acquire an image directly from a user of the apparatus 100 for image segmentation.

Specifically, a source of the image to be segmented may be different depending on which of a training process, verification process, or actual use process of the segmentation model the image is used in. For example, the apparatus 100 for image segmentation may use an open source dataset on the web in the case of the image used in the training process and the verification process, and may use an image directly input from the user of the apparatus 100 for image segmentation in the case of the image used in the actual use process.

The segmentation performer 120 performs segmentation on one or more images acquired by the acquirer 110 using a segmentation model which is deep learned through a plurality of images.

In addition, the segmentation model is characterized by being a U-Net-based model including a first type module based on depth-wise separable convolution (DSC) and a second type module based on a global context network (GCNet).

As such, significant advantages can be expected in image segmentation by applying the first type module and the second type module described above to the segmentation model, and thus features and advantages of the segmentation model of the present disclosure compared to the conventional model are as follows.

Conventionally, SegNet, U-Net, 2D Dense U-Net, etc. have been proposed as convolutional network-based image segmentation models. In particular, U-Net has become a representative model used for segmentation of medical-related images. However, in the conventional models including U-Net, it is difficult to change the number of channels of a feature map that goes through the convolution layer more than a certain amount and a receptive field does not reflect the non-local feature as down sampling is performed continuously during an encoding process. Accordingly, the conventional models have limitations in that the size and boundary of a segmented region in the image are not clear.

On the other hand, the segmentation model of the apparatus 100 for image segmentation can easily change the number of channels of the feature map that goes through the convolution layer through the first type module based on the DSC, and may derive segmentation results reflecting the non-local features despite continuous down sampling through the second type module based on the GCNet.

In the following embodiments, the architecture of the segmentation model including the first type module and the second type module will be described in more detail.

According to an embodiment, when the tomographic image of the brain obtained by the magnetic resonance imaging (MRI) is acquired by the acquirer 110, the segmentation performer 120 may segment the tomographic image of the brain into a plurality of sections, and determine one or more sections satisfying a preset condition among the plurality of sections as a stroke lesion.

According to an embodiment, the segmentation model may be the U-Net-based model in which at least some of a plurality of convolution layer blocks in the segmentation model are replaced with the first type module.

Specifically, the first type module may replace all of the plurality of convolution layer blocks constituting the encoder in which down sampling is performed and the decoder in which up sampling is performed in the segmentation model.

Also, according to an embodiment, the first type module may include a plurality of depth-wise convolution layer blocks for extracting feature information of a feature map and a plurality of point-wise convolution layer blocks for controlling the number of channels of the feature map.

Specifically, the first type module may calculate a map for extracting feature information by repeatedly applying the depth-wise convolution layer block and the point-wise convolution layer block to a feature map which is input to the first type module, calculate a map for controlling the number of channels by applying only the point-wise convolution layer block to the feature map which is input to the first type module, and sum the calculated map for extracting the feature information and the calculated map for adjusting the number of channels and output a result of the summation. In this regard, description will be made later in detail with reference to FIG. 4 below.

Meanwhile, according to an embodiment, the segmentation model may be the U-Net-based model in which the second type module is disposed between the encoder and the decoder in the segmentation model.

Specifically, the second type module may be disposed between the first type module disposed in the deepest layer of the encoder and the first type module disposed in the deepest layer of the decoder.

Also, according to one embodiment, the second type module may include a first convolution layer block for extracting feature information of a feature map, a second convolution layer block, and a global context block (GC-Block) based on the global context network.

Specifically, the second type module may calculate a global feature map by applying the first convolution layer block, the second convolution layer block, and the global context block to a feature map which is input to the second type module, and sum the feature map which is input to the second type module and the global feature map and output a result of the summation. In this regard, description will be made later in detail with reference to FIG. 5 below.

In the illustrated embodiment, configurations may respectively have different functions and capabilities other than those described below, and additional configurations may be included in addition to those described below.

In addition, in an embodiment, the acquirer 110 and the segmentation performer 120 may be implemented using one or more physically separated devices, or implemented by one or more processors or a combination of one or more processors and software, and may not be clearly distinguished in a specific operation unlike the illustrated example.

Figure 2:
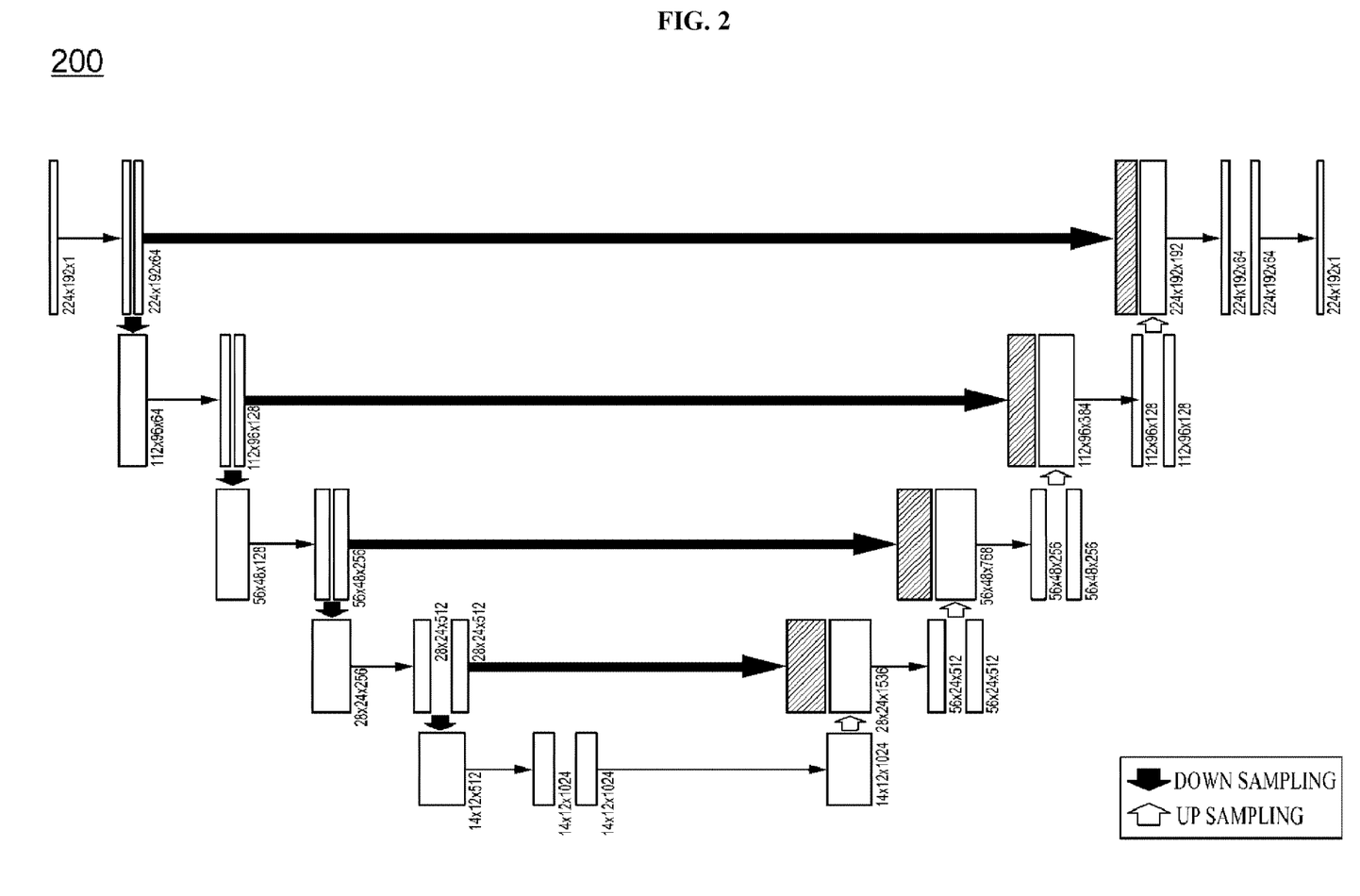
FIG. 2 is an exemplary diagram for describing a conventional U-Net architecture.

FIG. 2 is an exemplary diagram 200 for describing a conventional U-Net architecture. For convenience of description, the conventional U-Net architecture will be referred to as a 'conventional architecture' hereinafter.

Referring to FIG. 2, when an image having a size of 224*192 is input to the conventional architecture, a 3*3 convolution operation is performed twice by the first convolution layer block. In this case, padding may be applied to prevent a decrease in the size of the output feature map, and as a result, the number of channels of the feature map output from the first convolution layer block may increase to 64 channels. However, it should be noted that this is an example, and the size and number of convolution filters applied to an input image, a padding value, etc. may be different depending on the embodiment.

After that, the feature map output from the first convolution layer block may be subjected to down sampling and processed to a size of 112*96*64, may be repeatedly subjected to a process of 3*3 convolution operation, padding, and down sampling several times by the convolution layer block at several stages and may be processed into a feature map having a size of 56*48*128, 28*24*256, 14*12*512, etc.

After that, the conventional architecture may generate an output image having the same size as the input image by continuously repeating the process of up sampling, 3*3 convolution operation, and padding on the feature map having the size of 14*12*1024 that was last processed on the encoder.

In this case, in the conventional architecture, a feature map having sizes of 112*96*128, 56*48*256, 28*24*512, etc. before having been subjected to down sampling may be concatenated with an upsampled feature map using a skip connection technique.

However, in such a conventional architecture, since convolution operations should be performed twice for each convolution layer block, there is a disadvantage in that too many training parameters are required according to the size of each convolution filter, the number of filters, and the number of channels of the input feature map (or image). For this reason, a model having the conventional architecture requires excessive resources during training, and thus has an architectural problem in which training efficiency and performance after training are deteriorated.

Figure 3:
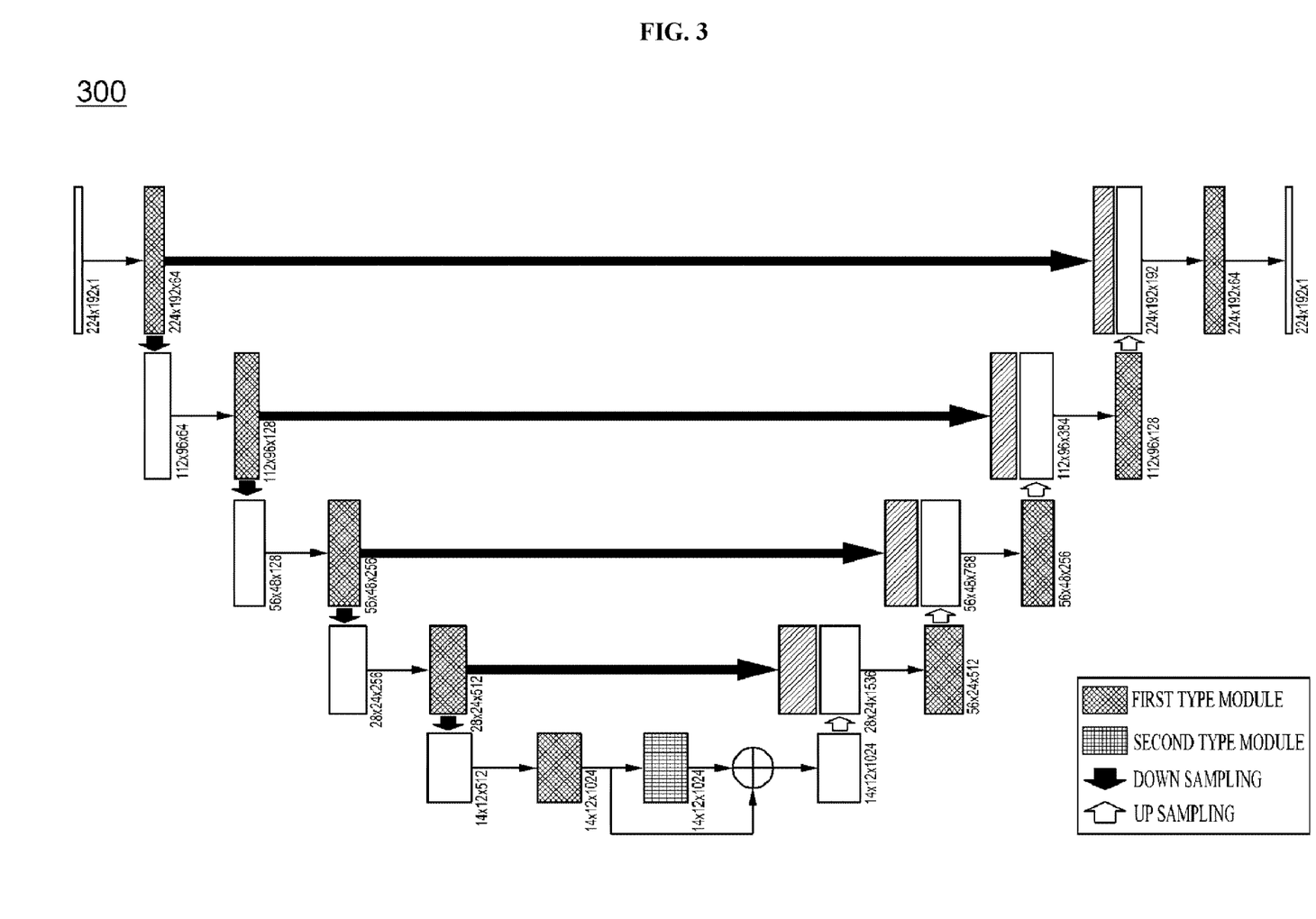
FIG. 3 is an exemplary diagram for describing in detail an architecture of a segmentation model according to an embodiment.

FIG. 3 is an exemplary diagram 300 for describing in detail the architecture of the segmentation model according to an embodiment.

Similar to the conventional architecture of FIG. 2, the segmentation model illustrated in FIG. 3 generates a feature map having the size of 14*12*1024 by repeatedly applying the process of 3*3 convolution operations, padding, and down sampling twice to a received image having a size of 224*192.

However, the process of 3*3 convolution operation, padding, and down sampling is performed by the first type module instead of the conventional convolution layer block, and thus the first type module not only extracts feature information of the feature map through the depth-wise convolution layer block, but also adjusts the number of channels of the feature map through the point-wise convolution layer block, thereby capable of dramatically reducing the number of training parameters of the segmentation model.

In addition, unlike the conventional architecture in which up sampling is applied to a feature map having the size of 14*12*1024 right away, the segmentation model may generate an output image that effectively reflects the non-local features of the input image by summing the feature map having the size of 14*12*1024 immediately after having gone through the encoder and the feature map having the size of 14*12*1024 that has been additionally gone through the second type module by element and applying up sampling.

Figure 4:
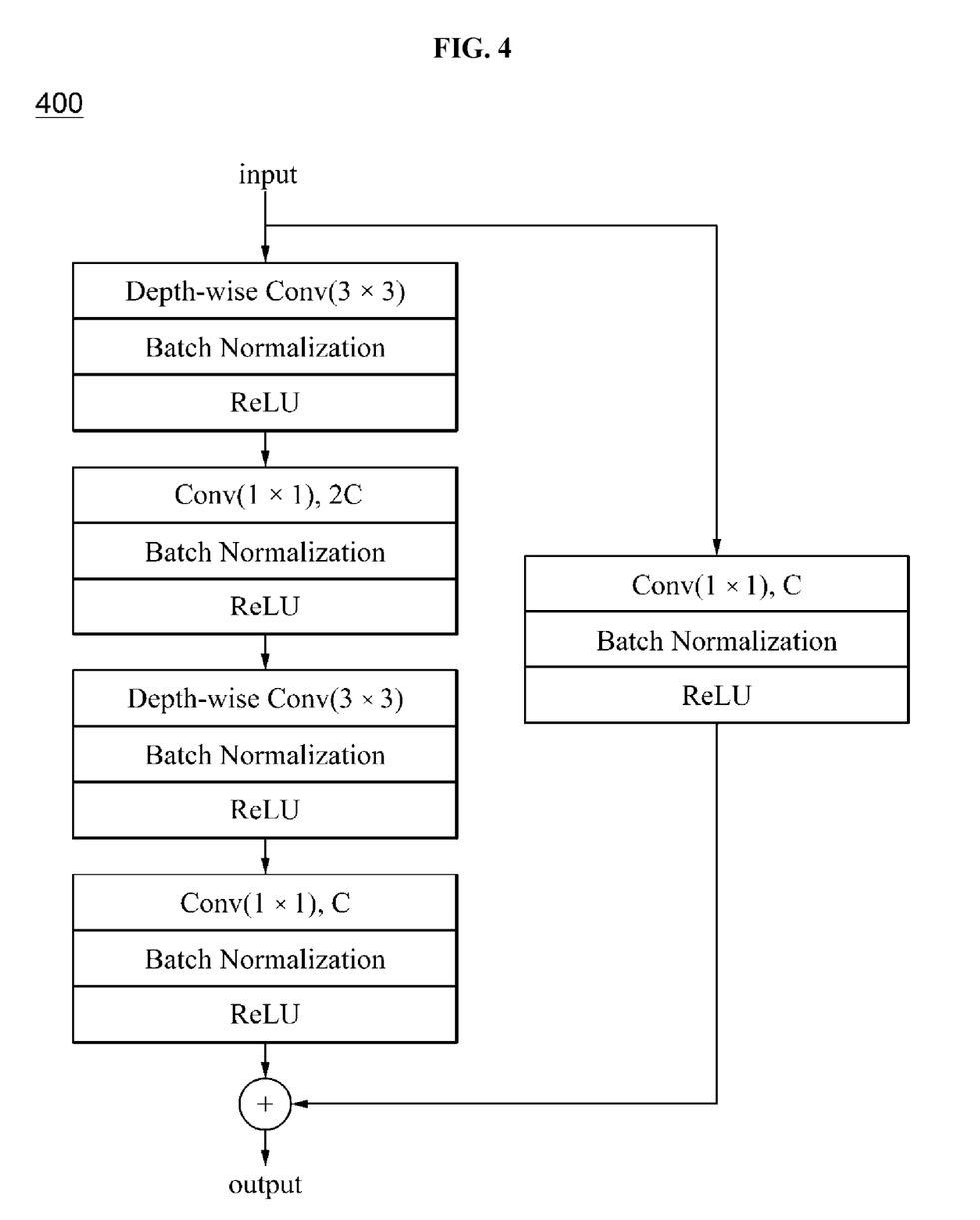
FIG. 4 is an exemplary diagram for describing in detail a first type module according to an embodiment.

FIG. 4 is an exemplary diagram 400 for describing in detail the first type module according to an embodiment.

In the following embodiments, the depth-wise convolution layer block means a layer block including a 3*3 depth-wise convolution layer block, a batch normalization layer for performing batch normalization, and an activation function layer for applying a ReLU activation function. In addition, the point-wise convolution layer block means a layer block including a 1*1 convolution layer for controlling the number of channels, a batch normalization layer, and an activation function layer.

Referring to FIG. 4, the first type module calculates a map for extracting feature information by repeatedly applying the depth-wise convolution layer block and the point-wise convolution layer block to the input feature map twice, calculates a map for controlling the number of channels by applying only the point-wise convolution layer block once to the input feature map, and then sums the calculated map for extracting feature information and calculated map for controlling the number of channels by element and output a result of the summation as an output of the first type module.

Specifically, the first type module adjusts the number of output channels to C using the point-wise convolution layer block in the process of calculating the map for adjusting the number of channels. Meanwhile, in the process of calculating the map for extracting feature information, the first type module increases the number of output channels to 2C using the first point-wise convolution layer block, and then adjusts the number of output channels to C again using the second point-wise convolution layer block. In this case, it should be noted that the number of output channels increased by using the first point-wise convolution layer block may be set in various ways, and is not necessarily limited to 2C.

With this configuration, the first type module may extract more various feature information from the feature map according to the number of channels increased in the middle, and at the same time, reduce the number of training parameters compared to the conventional architecture by adjusting the number of output channels using the point-wise convolution layer block.

For example, it is assumed that k is the size of the filter used for convolution operation, $C_i$ is the number of channels of an input feature map, $C_O$ is the number of channels of an output feature map, and $C_{E0}$ is the number of channels of a feature map output from the encoder to the decoder. In this case, according to the conventional architecture, the number of training parameters corresponding to one convolution layer block positioned in the encoder is $(C_i*k^2*C_o)+(C_o*k^2*C_o)$, which results in a total of $k^2*C_o*(C_i+C_o)$, and the number of training parameters corresponding to one convolution layer block positioned in the decoder is $(C_i*k^2*C_o)+((C_{E0}+C_o)*k^2*C_o)+(C_o*k^2*C_o)$, which results in a total of $k^2*C_o*(C_i+C_o)$.

On the other hand, in the case of the segmentation model illustrated in FIG. 4, the number of training parameters corresponding to one first type module positioned in the encoder is $(C_i*k^2)+(C_i*2C_0)+(2C_0*k^2)+(2C_0*C_0)+(C_i*C_0)$, which results in a total of $k^2*(C_i+2C_0)+C_0*(3C_i+2C_0)$, and the number of training parameters corresponding to one first type module positioned in the decoder is $((C_{E0}+C_i)*k^2)+((C_{E0}+C_i)*2C_0)+(2C_0*k^2)+(2C_0*C_0)+((C_{E0}+C_i)*C_0)$, which results in a total of $k^2*(C_{E0}+C_i+C_0)+C_0*(3C_{E0}+3C_i+2C_0)$. In addition, the number of training parameters corresponding to the second type module to be described later is $$\left(Ci*\frac{C_i}{8}*k^2\right)+\left(\frac{C_i}{8}*1\right)+\left(\frac{C_i}{8}*\frac{C_i}{16}\right)+\left(\frac{C_i}{8}*\frac{C_i}{16}\right)+\left(Ci*\frac{C_i}{8}*k^2\right),$$

which results in a total of $$\frac{1}{8}k^2*Ci+\frac{1}{8}Ci*\left(1+\frac{C_i}{8}\right).$$

Accordingly, when the numerical values shown in FIGS. 2 and 3 are substituted, the total number of training parameters of the conventional architecture is about 34.5 million, whereas the total number of training parameters of the segmentation model of FIG. 4 is about 11.5 million. Therefore, it can be seen that the segmentation model reduces the number of training parameters related to convolution operations performed twice by about 3 times compared to the conventional architecture by replacing the convolution layer block of the conventional architecture with the first type module.

Figure 5:
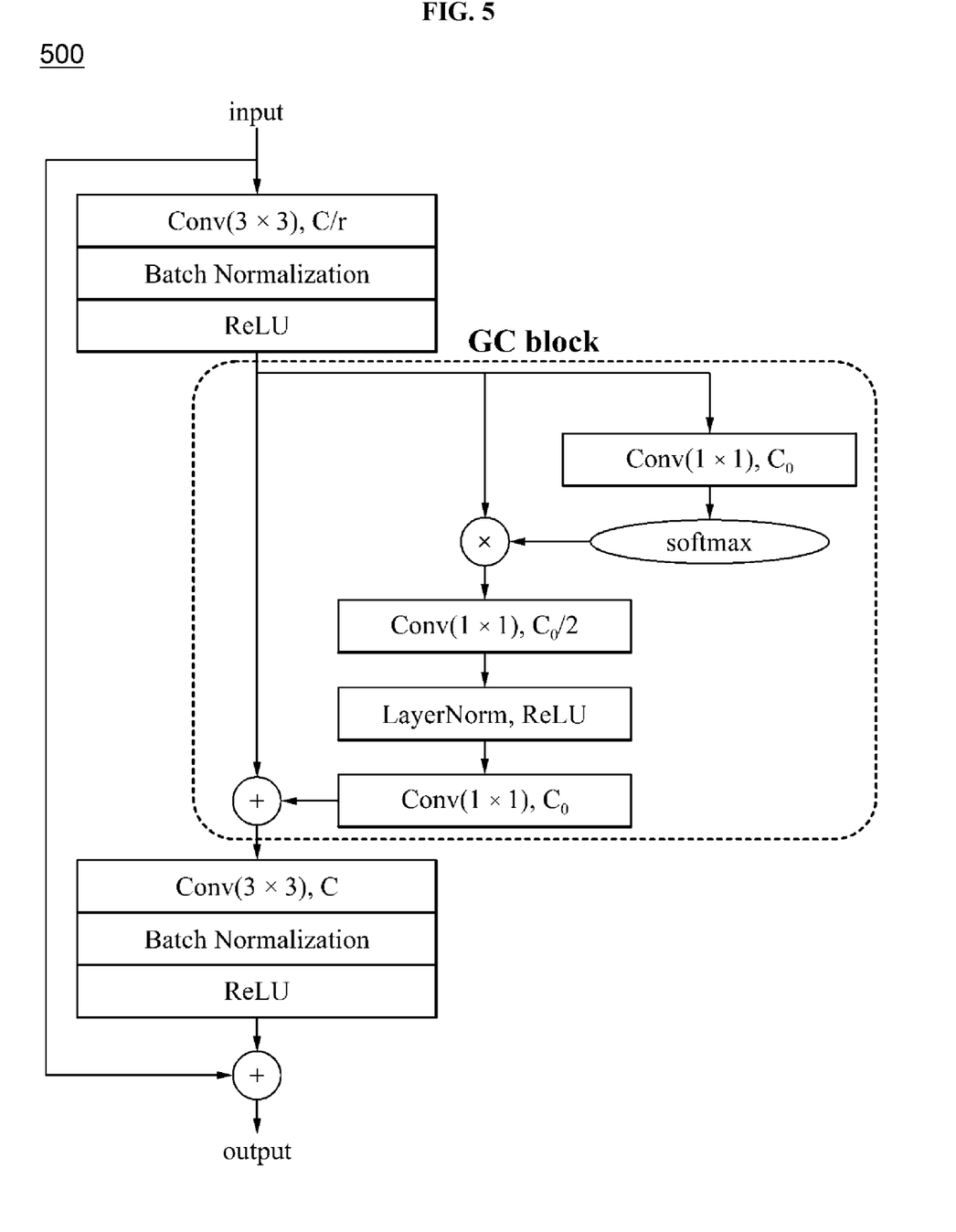
FIG. 5 is an exemplary diagram for describing in detail a second type module according to an embodiment.

FIG. 5 is an exemplary diagram 500 for describing in detail the second type module according to an embodiment.

In the following embodiment, the first convolution layer block and the second convolution layer block mean layer blocks including the 3*3 depth-wise convolution layer block, the batch normalization layer for performing batch normalization, and the activation function layer for applying the ReLU activation function.

Referring to FIG. 5, the second type module calculates a global feature map by applying the first convolution layer block, the second convolution layer block, and the global context block to the input feature map, and then sums the calculated global feature map and the previously input feature map by element and outputs a result of the summation as an output of the second type module.

Specifically, the second type module may input the feature map having the number of channels of C to the first convolution layer block, input the output of the first convolution layer block to the global context block, input the output of the global context block to the second convolution layer block, sums the output of the second convolution layer block and the feature map input to the first convolution layer block by element, and output a result of the summation as the output of the second type module.

Among these, the first convolution layer block and the second convolution layer block may adjust the number of channels of an output feature map. Specifically, the first convolution layer block may reduce the number of channels of the input feature map to reduce an amount of computation, and the second convolution layer block may make the number of channels of the feature map that has gone through the second type module and the number of channels of the feature map input to the second type module coincident with each other.

In this regard, C/r and $C_O$ shown in FIG. 5 are the same value, and r may be a hyper parameter set by the user as a ratio of the number of channels to be reduced, or a training parameter determined by learning.

Meanwhile, the global context block may reflect the non-local context feature in the feature map input to the first convolution layer block through the following three configurations as illustrated in FIG. 5.

(1) Context feature extraction (context modeling): After one round of 1*1 convolution operation, the Softmax function is applied to calculate an attention weight, and the result thereof and the output of the first convolution layer block are subjected to matrix multiplication (2) Bottleneck transformation: After reducing the number of output channels to one half thereof first by using a 1*1 convolution operation, a process of layer normalization and activation function application is performed, and the number of output channels is restored through the 1*1 convolution operation again.

(3) Feature integration: The output of the first convolution layer block and the feature map generated in (2) are again summed by element FIG. 6 is a flowchart illustrating a method for image segmentation according to an embodiment.

Figure 6:
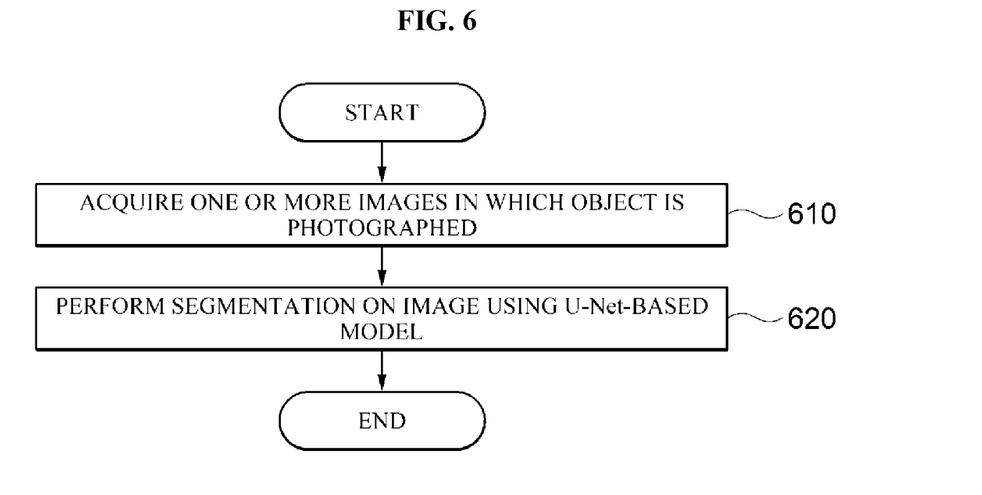
FIG. 6 is a flowchart illustrating a method for image segmentation according to an embodiment.

The method illustrated in FIG. 6 may be performed, for example, by the apparatus 100 for image segmentation described above.

First, the apparatus 100 for image segmentation 100 acquires one or more images in which an object is photographed (610).

Thereafter, the apparatus 100 for image segmentation performs segmentation on the one or more images acquired by using the segmentation model which is deep learned through a plurality of images (620).

In this case, the segmentation model is characterized by being the U-Net-based model including the first type module based on the depth-wise convolution layer block and and the second type module based the point-wise convolution layer block.

In the illustrated flowchart, although the method has been described by dividing the method into a plurality of steps, at least some steps may be performed in a different order, performed together in combination with other steps, omitted, performed by dividing the steps into sub-steps, or performed by being added with one or more steps (not illustrated).

Figure 7:
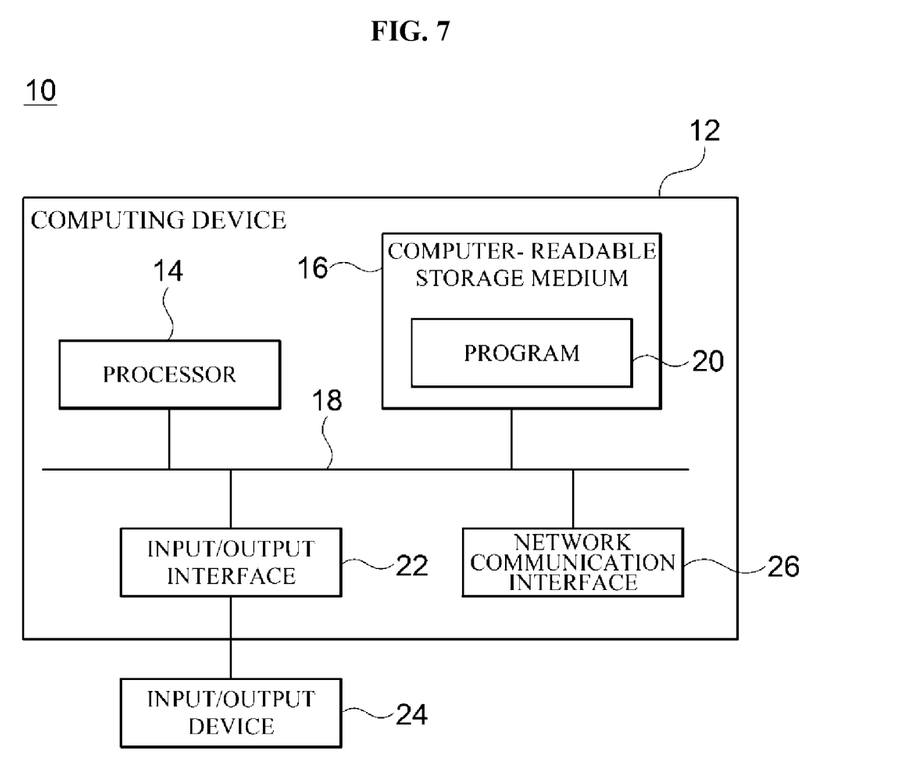
FIG. 7 is a block diagram illustratively describing a computing environment including a computing device according to an embodiment.

FIG. 7 is a block diagram illustratively describing a computing environment 10 including a computing device according to an embodiment. In the illustrated embodiment, respective components may have different functions and capabilities other than those described below, and may include additional components in addition to those described below.

The illustrated computing environment 10 includes a computing device 12. In an embodiment, the computing device 12 may be the apparatus 100 for image segmentation.

The computing device 12 includes at least one processor 14, a computer-readable storage medium 16, and a communication bus 18. The processor 14 may cause the computing device 12 to operate according to the exemplary embodiment described above. For example, the processor 14 may execute one or more programs stored on the computer-readable storage medium 16. The one or more programs may include one or more computer-executable instructions, which, when executed by the processor 14, may be configured so that the computing device 12 performs operations according to the exemplary embodiment.

The computer-readable storage medium 16 is configured so that the computer-executable instruction or program code, program data, and/or other suitable forms of information are stored. A program 20 stored in the computer-readable storage medium 16 includes a set of instructions executable by the processor 14. In one embodiment, the computer-readable storage medium 16 may be a memory (volatile memory such as a random access memory, non-volatile memory, or any suitable combination thereof), one or more magnetic disk storage devices, optical disk storage devices, flash memory devices, other types of storage media that are accessible by the computing device 12 and capable of storing desired information, or any suitable combination thereof.

The communication bus 18 interconnects various other components of the computing device 12, including the processor 14 and the computer-readable storage medium 16.

The computing device 12 may also include one or more input/output interfaces 22 that provide an interface for one or more input/output devices 24, and one or more network communication interfaces 26. The input/output interface 22 and the network communication interface 26 are connected to the communication bus 18. The input/output device 24 may be connected to other components of the computing device 12 through the input/output interface 22. The exemplary input/output device 24 may include a pointing device (such as a mouse or trackpad), a keyboard, a touch input device (such as a touch pad or touch screen), a speech or sound input device, input devices such as various types of sensor devices and/or photographing devices, and/or output devices such as a display device, a printer, a speaker, and/or a network card. The exemplary input/output device 24 may be included inside the computing device 12 as a component constituting the computing device 12, or may be connected to the computing device 12 as a separate device distinct from the computing device 12.

The embodiments described above may be implemented by a hardware component, a software component, and/or a combination of a hardware component and a software component. For example, the apparatuses, methods, and components described in the embodiments may be implemented using one or more general purpose or special purpose computers, such as, for example, a processor, controller, arithmetic logic unit (ALU), digital signal processor, microcomputer, field programmable gate array (FPGA), programmable logic unit (PLU), microprocessor, or any other device capable of executing and responding to an instruction. A processing device may execute an operating system (OS) and one or more software applications running on the operating system. The processing device may also access, store, manipulate, process, and generate data in response to execution of software. For convenience of understanding, although a description that one processing device is used may have been made, a person of ordinary skill in the art will recognize that the processing device may include a plurality of processing elements and/or a plurality of types of processing elements. For example, the processing device may include a plurality of processors, or one processor and one controller. Other processing configurations, such as parallel processors, are also possible.

Software may include a computer program, code, instruction, or combinations of one or more of these, which may configure the processing device to operate as desired, or instruct the processing device independently or collectively. Software and/or data may be permanently or temporarily embodied in any tangible machine, component, physical equipment, virtual equipment, computer storage medium or device, or signal wave being transmitted, in order to be interpreted by the processing device or to provide instructions or data to the processing device. Software may be distributed over networked computer systems and stored or executed in a distributed manner. Software and data may be stored in one or more computer-readable recording media.

Although representative embodiments of the present disclosure have been described in detail, a person skilled in the art to which the present disclosure pertains will understand that various modifications may be made thereto within the limits that do not depart from the scope of the present disclosure. Therefore, the scope of rights of the present disclosure should not be limited to the described embodiments, but should be defined not only by claims set forth below but also by equivalents to the claims.

What is claimed is:

1. An apparatus for image segmentation, which is implemented with a computing device that includes one or more processors and a memory for storing one or more programs executed by the one or more processors, the apparatus comprising:
   an acquirer configured to acquire one or more images in which an object is photographed; and
   a segmentation performer configured to perform segmentation on the one or more images using a segmentation model which is deep learned through a plurality of images,
   wherein the segmentation model is a U-Net-based model including a first type module based on depth-wise separable convolution (DSC) and a second type module based on global context network (GCNet),
   wherein the first type module is configured to include a plurality of depth-wise convolution layer blocks for extracting feature information of a feature map and a plurality of point-wise convolution layer blocks including a first point-wise convolution layer block and a second point-wise convolution layer block for controlling a number of channels of the feature map,
   wherein the first type module is configured to:
      calculate a map for extracting feature information by repeatedly applying the depth-wise convolution layer block and the point-wise convolution layer block to an input feature map, and increase a number of output channels by using the first point-wise convolution layer block and then adjust the increased number of the output channels to the number before increasing by using the second point-wise convolution layer block;
      calculate a map for controlling the number of channels by applying only the point-wise convolution layer blocks to the input feature map; and
      sum the map for extracting the feature information and the map for adjusting the number of channels and output a result of the summation.

2. The apparatus of claim 1, wherein the one or more images include a tomographic image of a brain obtained by magnetic resonance imaging (MRI).

3. The apparatus of claim 2, wherein the segmentation performer is configured to segment the tomographic image of the brain into a plurality of sections, and determine one or more sections satisfying a preset condition among the plurality of sections as a stroke lesion.

4. The apparatus of claim 1, wherein the segmentation model is a U-Net-based model in which at least some of a plurality of convolution layer blocks in the segmentation model are replaced with the first type module.

5. The apparatus of claim 1, wherein the segmentation model is a U-Net-based model in which the second type module is disposed between an encoder in which down sampling is performed and a decoder in which up sampling is performed in the segmentation model.

6. The apparatus of claim 1, wherein the second type module is configured to include a first convolution layer block for extracting feature information of a feature map, a second convolution layer block, and a global context block (GCBlock) based on the global context network.

7. The apparatus of claim 6, wherein the second type module is configured to:
   calculate a global feature map by applying the first convolution layer block, the second convolution layer block, and the global context block to an input feature map; and
   sum the input feature map and the global feature map and output a result of the summation.

8. A method for image segmentation performed by a computing device that includes one or more processors and a memory for storing one or more programs executed by the one or more processors, the method comprising:
   acquiring one or more images in which an object is photographed; and
   performing segmentation on the one or more images using a segmentation model which is deep learned through a plurality of images,
   wherein the segmentation model is a U-Net-based model including a first type module based on depth-wise separable convolution (DSC) and a second type module based on global context network (GCNet),
   wherein the first type module is configured to include a plurality of depth-wise convolution layer blocks for extracting feature information of a feature map and a plurality of point-wise convolution layer blocks including a first point-wise convolution layer block and a second point-wise convolution layer block for controlling the number of channels of the feature map,
   wherein the first type module is configured to:
      calculate a map for extracting feature information by repeatedly applying the depth-wise convolution layer block and the point-wise convolution layer block to an input feature map, and, in calculating the map for extracting feature information, increase a number of output channels using a first point-wise convolution layer block of the plurality of point-wise convolution layer blocks and then adjust the increased number of the output channels to the number before increasing by using a second point-wise convolution layer block;
calculate a map for controlling the number of channels by applying only the point-wise convolution layer block to the input feature map; and
sum the map for extracting the feature information and the map for adjusting the number of channels and output a result of the summation.

9. The method of claim 8, wherein the one or more images include a tomographic image of a brain obtained by magnetic resonance imaging (MRI).

10. The method of claim 9, wherein in the performing of segmentation, the tomographic image of the brain is segmented into a plurality of sections, and one or more sections satisfying a preset condition among the plurality of sections is determined as a stroke lesion.

11. The method of claim 8, wherein the segmentation model is a U-Net-based model in which at least some of a plurality of convolution layer blocks in the segmentation model are replaced with the first type module.

12. The method of claim 8, wherein the segmentation model is a U-Net-based model in which the second type module is disposed between an encoder in which down sampling is performed and a decoder in which up sampling is performed in the segmentation model.

13. The method of claim 8, wherein the second type module is configured to include a first convolution layer block for extracting feature information of a feature map, a second convolution layer block, and a global context block (GCBlock) based on the global context network.

14. The method of claim 13, wherein the second type module is configured to:
calculate a global feature map by applying the first convolution layer block, the second convolution layer block, and the global context block to an input feature map; and
sum the input feature map and the global feature map and output a result of the summation.

* * * * *